United States Patent [19]

Lang et al.

[11] Patent Number: 4,849,444
[45] Date of Patent: Jul. 18, 1989

[54] BENZENESULFONAMIDE DERIVATIVES AND A PROCESS FOR THE MEDICAL USE THEREOF

[75] Inventors: Hans-Jochen Lang, Hofheim am Taunus; Max Hropot, Flörsheim am Main; Ernold Granzer, Kelkheim; Bela Kerekjarto, Hofheim am Taunus, all of Fed. Rep. of Germany

[73] Assignee: Hoechst Aktiengesellschaft, Frankfurt am Main, Fed. Rep. of Germany

[21] Appl. No.: 184,963

[22] Filed: Apr. 22, 1988

[30] Foreign Application Priority Data

Apr. 24, 1987 [DE] Fed. Rep. of Germany ....... 3713757

[51] Int. Cl.$^4$ .................... C07D 207/26; A61K 31/40
[52] U.S. Cl. ..................................... 514/425; 548/545
[58] Field of Search ........................ 548/545; 514/425

[56] References Cited

U.S. PATENT DOCUMENTS 4,235,918 11/1980 Lang et al. ..................... 424/274

Primary Examiner—David B. Springer
Attorney, Agent, or Firm—Finnegan, Henderson, Farabow, Garrett & Dunner

[57] ABSTRACT

Compounds of the formula I

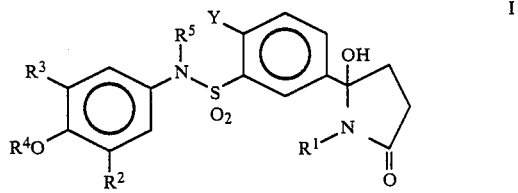

with $R^1$ equal to H or (cyclo)alk(en)yl, $R^2$ equal to H or alkyl, $R^3$ equal to alkyl, $R^4/R^5$ equal to H, alkyl or acyl, and Y equal to H, alkyl, $CF_3$ or Hal, are described, as are processes for the preparation thereof.

They are effective diuretics and antihypertensive agents with a lipid-lowering action.

8 Claims, No Drawings

BENZENESULFONAMIDE DERIVATIVES AND A PROCESS FOR THE MEDICAL USE THEREOF

The invention relates to benzenesulfonamide derivatives.

It is known that benzenesulfonamide derivatives of the formula XII

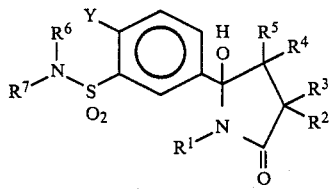

have a strong diuretic and saluretic action (U.S. Pat. No. 4,235,918). However, in these known compounds $R^7$ is not optionally substituted phenyl.

The known compounds are still not entirely satisfactory for many purposes, especially for the treatment of hypertension in elderly people.

Hence the invention has the object of making available benzenesulfonamide derivatives whose properties have been further improved and whose activity exceeds that of the known compounds XII.

This has been achieved by benzenesulfonamide derivatives of the formula I

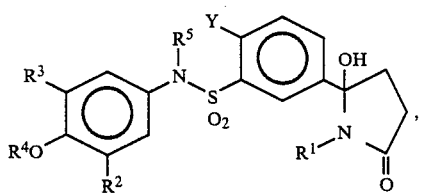

in which
$R^1$ denotes hydrogen, alkyl or alkenyl having 1-4 carbon atoms, or cycloalkyl having 3 to 5 ring members,
$R^2$ denotes hydrogen or an alkyl radical having 1 to 6 carbon atoms
$R^3$ denotes an alkyl radical having 3 to 5 carbon atoms,
$R^4$ and $R^5$ denote hydrogen, a $(C_1-C_3)$-alkyl radical or an acyl radical of an aliphatic carboxylic acid having 1 to 3 carbon atoms, and
Y denotes hydrogen, methyl, trifluoromethyl, F or Cl, as well as the open-chain tautomeric forms correspondinto to I, of the formula Ia

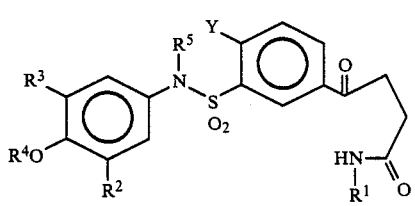

in which $R^1$ to $R^5$ and Y have the indicated meaning.

Preferred compounds of the formula I are those in which $R^4$ and $R^5$ denote hydrogen, and Y denotes chlorine.

Particularly preferred compounds of the formula I are those in which $R^4$ and $R^5$ represents hydrogen, Y represents chlorine, and $R^2$ and $R^3$ denote methyl, isopropyl and/or tert.-butyl, but where $R^3$ contains at least 3 carbon atoms and is branched.

Those in which $R^1$ has the meaning of methyl are of particularly outstanding importance.

Outstanding individual compounds which should be mentioned are:
5-[4-chloro-3-(3,5-diisopropyl-4-hydroxyphenylsulfamoyl)phenyl]-5-hydroxy-1-methyl-2-pyrrolidone and
5-[4-chloro-3-(3,5-di-tert.-butyl-4-hydroxyphenylsulfamoyl)phenyl]-5-hydroxy-1-methyl-2-pyrrolidone.

The invention also relates to a process for the preparation of the compounds of the formula I, which comprises (a) reaction of compounds of the formula II

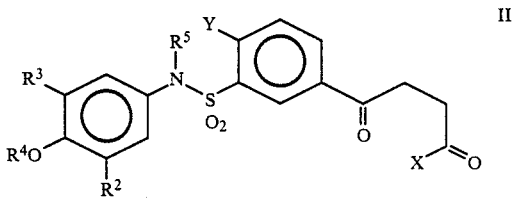

with a primary amine of the formula III in a customary manner $$R^1-NH_2 \quad \quad III$$

where $R^1$ to $R^5$ and Y have the indicated meaning, and X is the reactive inorganic or organic radical of the carboxylic acid (X=OH), or (b) reaction of compounds of the formula IV

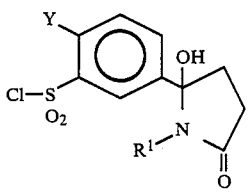

with an amine of the formula V

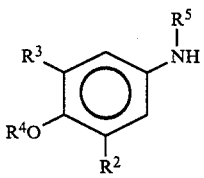

in which $R^1$ to $R^5$ and Y have the indicated meaning, and conversion, where appropriate, of the compounds of the formula I which have been obtained by route (a) and (b) and in which $R^4$ and/or $R^5$ denote hydrogen, by customary alkylation or acylation, into compounds of the formula I in which $R^4$ and/or $R^5$ have one of the other meanings indicated above.

The compounds of the formula IV can also, in analogy to the equilibrium I Ia, exist in their open-chain tautomeric forms IVa:

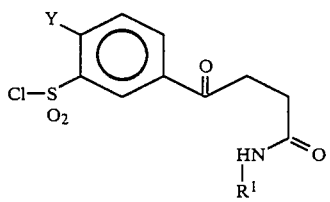

Which of the two tautomeric forms I or Ia of a compound according to the invention predominates in the equilibrium formulated below

depends on the solvent and the temperature, but especially on the substituent $R^1$.

The compounds of the formula I according to the invention can also exist in their possible geometrically isomeric structures.

The alkyl radicals in the substituents $R^1$ to $R^5$ can be both straight-chain and branched.

The procedure designated a) is advantageously carried out in such a way that, for example, compounds of the formula II in which $R^2$ to $R^5$ and Y have the indicated meaning, and X is the O-($C_1$-$C_4$)-acyl radical of a mixed anhydride, are reacted with amines of the formula III. The mixed anhydrides are advantageously generated in situ by converting compounds of the formula VI

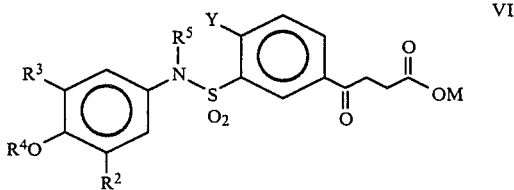

in which M denotes hydrogen, with one equivalent of a suitable base, for example with an alkali metal or an alkaline earth metal hydroxide such as KOH, NaOH or $Ca(OH)_2$ with an alkali metal carbonate or bicarbonate such as $Na_2CO_3$, $K_2CO_3$, $NaHCO_3$, $KHCO_3$ or with a, preferably tertiary, amine such as trimethylamine, triethylamine, tripropylamine, tributylamine or dicyclohexylethylamine, into the corresponding carboxylic salts of the formula VI in which M preferably represents Na, K, Ca or a trialkylammonium cation, such as $[HN(C_2H_5)_3]^+$, which are then reacted with 1–2.5 mole, preferably with 1 to 1.5 mole, of an activated acid derivative to give a mixed anhydride.

An activated acid derivative which is advantageously used is, for example, an alkyl chloroformate, preferably ethyl chloroformate or methyl chloroformate, a carbamoyl chloride (such as N,N-dimethylcarbamoyl chloride or N,N-diethylcarbamoyl chloride) or the chloride of an aliphatic or aromatic sulfonic acid, for example methane-, ethane-, benzene- or p-toluenesulfonyl chloride.

The reaction is advantageously carried out in an anhydrous polar organic solvent, for example in acetone, methyl ethyl ketone, a ($C_1$–$C_6$)-alkyl alkanoid, such as methyl or ethyl acetate, an alkanamide, for example dimethylformamide or dimethylacetamide, in dimethyl sulfoxide, in acetonitrile, in a lower aliphatic alcohol, for example in methanol, ethanol or isopropanol, preferably in a cyclic or open-chain ether and polyether such as tetrahydrofuran, dioxane, ethylene glycol dimethyl ether or diethylene glycol dimethyl ether. The reaction time for a 0.1 molar batch is 1 minute to 5 hours, with the mixture preferably being left to stir for a period of 5 to 60 minutes. The reaction can be carried out in a temperature range from −50° C. to 100° C., with between −30° C. and +30° C. being advantageous and between −10° C. and +15° C. being preferred.

Although the mixed anhydrides can be isolated by, for example, evaporating off the solvent at temperatures between −5° C. and +10° C., and extracting from the residue with a suitable solvent, such as ethyl acetate, it is advantageous to proceed in such a way that the mixed anhydride is not isolated and the amine of the formula III is added to the reaction mixture. The amine can be added both undiluted and in the form of a solution, it being possible and advantageous to use as solvent that in the reaction mixture or one of the solvents indicated for this purpose, as well as aqueous solutions of the amine or of ammonia. The amount of amine used for this, relative to the compound of the formula VI, is at least 1 mole, but is often advantageously a more marked molar excess (10-fold and more). The reaction is carried out in a temperature range between −30° C. and +100° C., preferably between +5° C. and +40° C. The reaction time is between 10 minutes and 5 days, it being possible to follow the progress of the reaction by thin-layer chromatography, advantageously on silica gel.

The acid chlorides of the formula II, in which X represents chlorine and which can be prepared from compounds of the formula VI with $COCl_2$, oxalyl chloride, $POCl_3$, $SOCl_2$, $PCl_3$ or $PCl_5$, are, in principle, reacted as the mixed anhydrides in the manner just described.

A variant, which is likewise advantageous, of procedure a) comprises reaction of the carboxylic acids of the formula VI with 1 mole of carbonyldiimidazole, with formation, under the indicated mild reaction conditions in an inert polar solvent, of the activated imidazolide of the carboxylic acid, of the formula II with X=1-imidazolyl, which can be converted, under conditions analogous to those for the mixed anhydride described above, with an amine of the formula III into the compounds of the formula I according to the invention.

Another advantageous variant of procedure a) comprises reaction of compounds of the formula II in which $R_2$ to $R_5$ and Y have the indicated meaning, and X denotes a lower alkoxy group having 1 to 6 carbon atoms in the alkyl moiety, preferably methoxy and ethoxy, or a phenyloxy radical which is optionally substituted by F, Cl or Br, with an amine of the formula III. The reaction is advantageously carried out in water or in a polar organic solvent which is inert towards amines, for example in a lower alkanamide such as dimethylformamide or dimethylacetamide, or dimethyl sulfoxide, or in a cyclic or open-chain ether or polyether such as tetrahydrofuran, dioxane or ethylene glycol dimethyl ether, but preferably in a lower alcohol such as methanol, ethanol, propanol or isopropanol, or in pure undiluted amine of the formula III without use of a solvent. The temperature range used is preferably 10° to 60° C., particularly preferably 15° to 30° C. The end of the reaction is advantageously determined by thin-layer chromatography on silica gel. Experience has shown that the reaction time depends on the reaction temperature and amine component used and is between one hour and 14 days, for example between 5 and 72 hours at room temperature. The carboxylic esters of the formula II and the amines of the formula III are preferably reacted in a molar ratio of 1:1 to 1:3, it also being possible, however, to use the amine in an up to 10-fold molar excess. The compound of the formula II in which $R_2$ to $R_5$ and Y have the indicated meaning, and X represents -O-$(C_1-C_6)$-alkyl, is obtained in a manner known per se by the action of a lower alkanol having 1 to 6 carbon atoms, preferably of methanol, ethanol, propanol, isopropanol and butanol, for example in the presence of an organic or inorganic acid chloride, by proton catalysis etc.

It is likewise possible to react in the same manner the corresponding activated esters of the formula II with X=CN, $N_3$ or $-O-CH_2CN$ with an amine of the formula III.

The amines of the formula III are known from the literature.

The compounds of the formula VI with M=H are obtained, for example, by Friedel-Crafts reaction of an aromatic compound VII with succinic anhydride to give compounds VIII

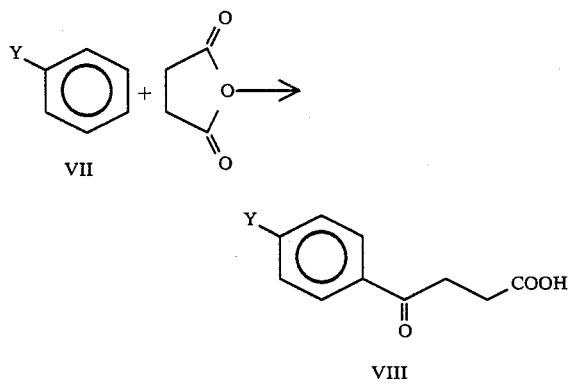

VII

VIII in which Y has the indicated meaning, and by subsequent nitration, reduction, diazotization and Meerwein reaction to give the compound IX

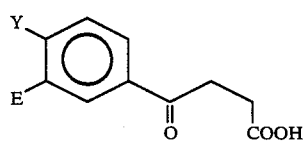

XI in which E is a $ClO_2S$ group and Y has the indicated meaning. The compounds of the formula IX are now reacted in a manner known per se with an aminophenol of the structure V, in which $R_2$ to $R_5$ have the indicated meaning, with the formation of the compounds VI. The procedure for this is preferably such that the two reactants are reacted in a molar ratio of 1:1 in water or in an inert polar organic solvent, as listed in detail above under process variant (a), or in mixtures of these solvents with water, and the progress of the reaction is followed by thin-layer chromatography on silica gel as stationary phase. It proves to be advantageous to have present at least 1, better 2 or more, moles of a suitable protoncutting auxiliary base as already listed in detail above, in particular pyridine or triethylamine, the reaction being carried out between $-15°$ and $+100°$ C., preferably between $20°$ and $+80°$ C.

In process b), sulfonyl chlorides of the formula IV are reacted with the aminophenols of the formula V. The procedure for this is such that, as already described for the preparation of the compounds IX, the two reactants are mixed in a molar ratio of 1:1 in water or in an inert polar organic solvent such as dimethylformamide, dimethylacetamide, dioxane, tetrahydrofuran, diethylene glycol dimethyl ether, in lower alcohols having 1–4 carbon atoms, for example in methanol, ethanol or isopropanol, as well as in a lower alkyl alkanoid, for example methyl or ethyl acetate, in the presence of an organic or inorganic auxiliary base. The bases already mentioned above are suitable for this, those preferably used being trialkylamines such as, for example, trimethylamine, triethylamine or ethyldicyclohexylamine, N,N-dimethylaniline, pyridine, alkali metal and alkaline earth metal carbonates or bicarbonates, such as sodium carbonate or sodium bicarbonate, or alkali metal and alkaline earth metal salts of weak alkanoic acid such as sodium acetate. The amines mentioned, for example pyridine, can also be used in excess to act simultaneously as solvent. The reaction can be carried out in a temperature range from $-30°$ C. to $+100°$ C., advantageously between $+10°$ C. and $+80°$ C., with the reaction time generally being at least 30 min but being complete after 2 days at the most. The sulfonyl halides of the formula IV, in which Hal preferably denotes chlorine, are preferably obtained by a 4-(3-aminophenyl)-4-oxobutyric acid of the formula X being activated, for example as described above using the mixed anhydride method with ethyl chloroformate in the presence of triethylamine, and converted with an amine of the formula III into the 5-(3-aminophenyl)-2-pyrrolidone derivatives of the formula XI. The compounds of the formula XI are then diazotized, preferably in aqueous hydrochloric acid and sodium nitrite, and immediately converted in situ, using a saturated solution of sulfur dioxide in glacial acetic acid and copper(II) chloride in a Meerwein-type reaction, into the sulfonyl chlorides of the formula IV.

Reaction diagram:

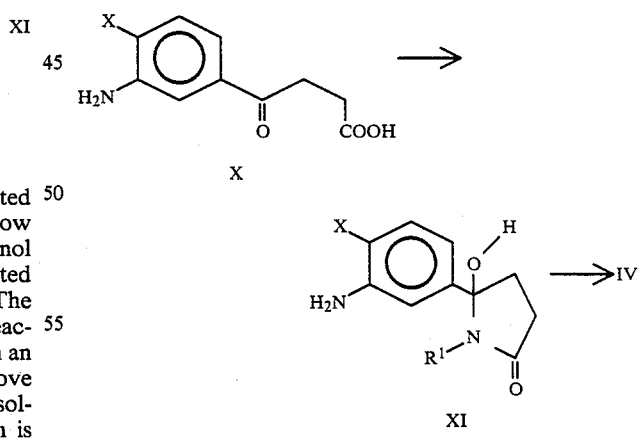

Apart from the benzenesulfonamide derivatives described in the examples, it is also possible to obtain according to the invention, for example, the compounds of the general formula I or Ia listed in the table which follows, with only the name of the cyclic tautomer of the formula I being specified hereinafter:

5-[4-Bromo-3-(3,5-diisopropyl-4-hydroxyphenylsulfamoyl)phenyl]-5-hydroxy-1-methyl-2-pyrrolidone.

5-[4-Bromo-3-(3,5-di-tert.butyl-4-hydroxyphenylsulfamoyl)phenyl]-5-hydroxy-1-methyl-2-pyrrolidone.

5-[3-(3,5-Diisopropyl-4-hydroxyphenylsulfamoyl)-4-trifluoromethylphenyl]-5-hydroxy-1-methyl-2-pyrrolidone.

5-[3-(3,5-Di-tert.butyl-4-hydroxyphenylsulfamoyl)-4-trifluoromethylphenyl]-5-hydroxy-1-methyl-2-pyrrolidone.

5-[4-Chloro-3-(3,5-di-tert.butyl-4-hydroxyphenylsulfamoyl)phenyl]-5-hydroxy-2-pyrrolidone.

5-[4-Chloro-3-(3,5-di-tert.butyl-4-hydroxyphenylsulfamoyl)phenyl]-1-ethyl-5-hydroxy-2-pyrrolidone.

The products of the process are valuable medicaments and are distiguished by a large number of very beneficial therapeutically utilizable properties, in particular by the combination of their very good diuretic and saluretic actions with pronounced and antiatherosclerotic properties.

This is of considerable therapeutic interest, especially because those lipid fractions (VLDL and LDL fractions) in the blood which are thought to be responsible for initiation or progression of atherosclerosis are either not diminished or even increased by the diuretics/saluretics hitherto commercially available, so that, especially in the latter case, active substances of these types have a certain atherogenic potential.

Diuretics are still, because of their numerous beneficial properties and their relatively good tolerability, among the basic therapeutics in the treatment of high blood pressure. Since high blood pressure in the elderly is, to a considerable extent, the consequence and initiator of atherosclerotic changes in vessels, which in turn intensify the high blood pressure, diuretic/saluretic active substances with a diminution in the risk of atherosclerosis are of particular therapeutic importance due to a reduction of, in particular, the atherogenic LDL fraction of cholesterol in the blood.

It was surprising that the compounds of the formula I, which differ from the known compounds of the formula XII by the introduction of a substituted phenyl radical on the aminosulfonyl group, have not only the diuretic and saluretic action but also an action lowering the serum level of the atherogenic lipid fractions. A profile of action of this type signifies a therapeutic advance in the treatment of hypertension in elderly people.

It is evident from numerous publications in recent years that the development of atherosclerotic plaques is preceded by injuries to the vascular endothelium. Endothelial injuries of this nature may be caused by fatty acid peroxides so that a diminution in these lipid peroxides, which are essentially transported in the LDL fraction, is necessarily associated with a diminution in the atherogenic risk. It has now been possible to show that the compounds according to the invention are able to suppress ($IC_{50}=5\times10^{-6}$ mol/l) the formation of malonaldehyde, which is a measure of lipid peroxidation. This antioxidant component of action is attributable to the hydroxyphenylamino substituent on the sulfonyl group of the compounds I.

The antihypertensive action of the compounds according to the invention, which can be detected in vitro on vascular muscle (isolated strips of aorta), proves to be surprisingly pronounced. The compounds inhibited the norepinephrine-induced contractions in isolated strips of aorta with an $IC_{50}=10^{-4}$ mol/l. They are among the most potent vasorelaxant diuretics in this model.

Thus the compounds according to the invention not only diminish the advance of atherosclerosis due to a reduction in the atherogenic cholesterol fraction and due to the lowering of the elevated blood pressure but also have a preventive action, due to the destruction of the lipid peroxides, to counter the formation of new atherosclerotic plaques.

In rats and monkeys, the new process products show a saluretic effect which is comparable to that of commercially available diuretics such as hydrochlorothiazide and chlorthalidone. Furthermore, the new process products are distinguished by a long-lasting duration of action. For this reason, the new process products are, as a consequence of their diuretic/saluretic action, also suitable for the treatment of hypertensive states, where appropriate being combined, as generally customary nowadays, with another antihypertensive agent.

The compounds I are administered in doses of at least 0.5 mg/kg and day, preferably 1 mg/kg and day, up to a maximum of 10 mg/kg/day, preferably up to 5 mg/kg/day, based on an adult person weighing about 75 kg.

Particularly suitable therapeutic formulations of the new compounds are tablets, coated tablets, capsules and suppositories, as well as ampuls for parenteral administration (i.v., s.c. and i.m.). The single therapeutic dose is between 0.5 and 500 mg, preferably between 10 and 300 mg, per tablet.

Apart from the customary extenders and vehicles, these formulations can, particularly for the treatment of high blood pressure, also contain an antihypertensive agent such as, for example, reserpine, hydralazine, guanethidine, α-methyldopa, clonidine, a β-sympatholytic active substance such as, for example, propranolol, or an ACE inhibitor such as captopril, enalapril or ramipril.

Also of interest are therapeutic combination products containing potassium-retaining compounds such as aldosterone antagonists, for example spironolactone, or pseudo aldosterone antiagonists such as triamterene or amiloride. Also suitable is potassium substitution in various administration forms, for example coated tablets, tablets, effervescent tablets, syrups, etc.

Combinations of the compounds according to the invention with an agent having antihyperuricemic and/or uricosuric activity may likewise be of therapeutic interest, which agent prevents pronounced increases of uric acid in the blood due to inhibition of xanthine oxidase or due to either an increase in the renal excretion of uric acid.

In the examples which follow, the melting and decomposition points of the examples are uncorrected.

EXAMPLE 1

5-[4-Chloro-3-(3,5-diisopropyl-4-hydroxyphenylsulfamoyl)phenyl]-5-hydroxy-1-methyl-2-pyrrolidone.

(a)

5-(3-Amino-4-chlorophenyl)-5-hydroxy-1-methyl-2-pyrrolidone 42.8 g of ethyl chloroformate are metered into a solution of 60 g of 4-(3-amino-4-chlorophenyl)-4-oxobutyric acid and 27.8 g of triethylamine in 500 ml of tetrahydrofuran in such a way that the temperature does not exceed 10° C. The mixture is stirred in the icebath for a further 10 min and then, while maintaining the cooling, a solution of 35 g of gaseous methylamine in 250 ml of tetrahydrofuran is added, during which a temperature of 25° C. should not be exceeded. After stirring for a further 45 minutes in the icebath, the solvent is removed by distillation, water is added to the residue, and the crystalline precipitate is filtered off. Crystals of melting point 154° C. (from ethanol).

(b) 5-(4-Chloro-3-chlorosulfonylphenyl)-5-hydroxy-1-methyl-2-pyrrolidone

A solution of 9.9 g of sodium nitrite in 60 ml of water is metered into, below the surface of, a solution of 30.5 g of 5-(3-amino-4-chlorophenyl)-5-hydroxy-1-methyl-2-pyrrolidone in 300 ml of half-concentrated hydrochloric acid at at 0° to 5° C. The reaction mixture is stirred while cooling for a further 10 min, and then a mixture of 15.2 g of copper(II)chloride dihydrate and 450 ml of a saturated solution of sulfur dioxide in glacial acetic acid is added in portions. The mixture is stirred for a further 30 min, and then the sulfonyl chloride is precipitated by addition of water, and the crystals are filtered off. Melting point 137°–139° C.

(c) 5-(4-Chloro-3-(3,5-diisopropyl-4-hydroxyphenylsulfamoyl)-phenyl)-5-hydroxy-1-methyl-2-pyrrolidone A suspension of 29.1 g of 4-amino-2,6-diisopropylphenol in 450 ml of ethyl acetate is added in portions to a solution of 17.5 g of 5-(4-chloro-3-chlorosulfonylphenyl)-5-hydroxy-1-methyl-2-pyrrolidone and 22.7 g of triethylamine in 200 ml of ethyl acetate. The mixture is stirred at 50° C. for 3 hours, cooled, water is added, the organic phase is separated off, and the aqueous phase is extracted several times with ethyl acetate. The combined organic phases are washed with water and dried over sodium sulfate, and the solvent is distilled off. After addition of about 250 ml of methylene chloride to the amorphous red residue it is refluxed and crystallization is induced by scratching. The mixture is stirred at room temperature for 30 min, and the precipitate is filtered off and recrystallized from acetonitrile without prolonged standing. Colorless crystals of melting point 198°–200° C.

EXAMPLE 2

5-[4-Chloro-3-(3,5-di-tert.butyl-4-hydroxyphenylsulfamoyl)phenyl]-5-hydroxy-1-methyl-2-pyrrolidone is obtained in analogy to the procedure indicated in Example 1(c) by reaction of 5-(4-chloro-3-chlorosulfonylphenyl)-5-hydroxy-1-methyl-2-pyrrolidone with 4-amino-2,6-di-tert.butylphenol in the presence of triethylamine. Colorless solid of melting point 120°–130° C.

EXAMPLE 3

5-[4-Chloro-3-(3-tert.butyl-4-hydroxy-5-methylphenylsulfamoyl)-phenyl]-5-hydroxy-1-methyl-2-pyrrolidone is obtained in analogy to the procedure indicated in Example 1(c) by reaction of 5-(4-chloro-3-chlorosulfonylphenyl)-5-hydroxy-1-methyl-2-pyrrolidone with 4-amino-2-tert.butyl-6-methylphenol in the presence of triethylamine. Colorless solid of melting point 120° C.

We claim:

1. A benzenesulfonamide derivative of the formula I

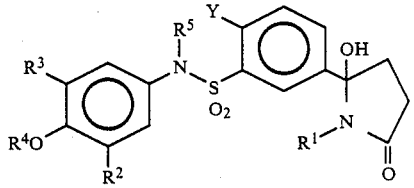

in which
R$^1$ denotes hydrogen, alkyl or alkenyl having 1-4 carbon atoms, or cycloalkyl having 3 to 5 ring members,
R$^2$ denotes hydrogen or an alkyl radical having 1 to 6 carbon atoms,
R$^3$ denotes an alkyl radical having 3 to 5 carbon atoms,
R$^4$ and R$^5$ denote hydrogen, a (C$_1$-C$_3$)-alkyl radical or an acyl radical of an aliphatic carboxylic acid having 1 to 3 carbon atoms, and
Y denotes hydrogen, methyl, trifluoromethyl, F or Cl.

2. A compound of the formula I as claimed in claim 1, wherein at least one of the substituents has the following meaning:
R$^1$ hydrogen, alkyl or alkenyl having 1-4 carbon atoms, or cycloalkyl having 3 to 5 ring members,
R$^2$ hydrogen or an alkyl radical having 1 to 6 carbon atoms,
R$^3$ an alkyl radical having 3 to 5 carbon atoms,
R$^4$ hydrogen,
R$^5$ hydrogen, and
Y chlorine.

3. A compound I as claimed in claim 1, wherein at least one of the substituents has the following meaning:
R$^1$ hydrogen, alkyl or alkenyl having 1-4 carbon atoms, or cycloalkyl having 3 to 5 ring members,
R$^2$ methyl, isopropyl or t-butyl,
R$^3$ isopropyl or t-butyl,
R$^4$ hydrogen,
R$^5$ hydrogen, and
Y chlorine.

4. A compound I as claimed in claim 1, wherein at least one of the substituents has the following meaning:
R$^1$ methyl,
R$^2$ methyl, isopropyl or t-butyl,
R$^3$ isopropyl or t-butyl,
R$^4$ hydrogen,
R$^5$ hydrogen, and
Y chlorine.

5. A compound I as claimed in claim 1, which is selected from the group comprising
5-[4-chloro-3-(3,5-diisopropyl-4-hydroxyphenylsulfamoyl)phenyl]-5-hydroxy-1-methyl-2-pyrrolidone and
5-[4-chloro-3-(3,5-di-tert.-butyl-4-hydroxyphenylsulfamoyl)-phenyl]-5-hydroxy-1-methyl-2-pyrrolidone.

6. The use of a compound I as claimed in claim 1 as a diuretic and antihypertensive agent with a lipid-lowering action.

7. The use of a compound I as claimed in claim 1 for the preparation of a medicament having a diuretic, antihypertensive and lipid-lowering action.

8. A pharmaceutical formulation composed of an effective amount of a compound I as claimed in claim 1 and pharmaceutically customary additives.

* * * * *